United States Patent [19]

Widlund et al.

[11] Patent Number: 5,797,895
[45] Date of Patent: Aug. 25, 1998

[54] METHOD OF BONDING AN ELASTIC MATERIAL TO A SUBSTRATE AND ARTICLE MANUFACTURED BY SAID METHOD

[75] Inventors: Urban Widlund, Mölnlycke; Robert Kling, Skene, both of Sweden

[73] Assignee: Molnlycke AB, Gothenburg, Sweden

[21] Appl. No.: 663,062

[22] PCT Filed: Dec. 21, 1994

[86] PCT No.: PCT/SE94/01236

§ 371 Date: Jun. 18, 1996

§ 102(e) Date: Jun. 18, 1996

[87] PCT Pub. No.: WO95/17296

PCT Pub. Date: Jun. 29, 1995

[30] Foreign Application Priority Data

Dec. 21, 1993 [SE] Sweden .................................. 9304232

[51] Int. Cl.$^6$ ..................................................... A61F 13/15
[52] U.S. Cl. .................. 604/385.2; 156/73.1; 156/73.2; 156/164; 428/326; 604/373

[58] Field of Search ................................. 156/73.1, 73.2, 156/161, 163, 164, 229; 428/230, 326; 604/373, 385.2, 387

[56] References Cited

U.S. PATENT DOCUMENTS

| 4,781,966 | 11/1988 | Taylor . | |
| 5,542,941 | 8/1996 | Morita | 604/387 |

FOREIGN PATENT DOCUMENTS

| 0 102 245 | 3/1984 | European Pat. Off. . |
| 0 115 286 | 8/1984 | European Pat. Off. . |
| 0 187 270 | 7/1986 | European Pat. Off. . |
| 0 217 032 | 4/1987 | European Pat. Off. . |
| 0 281 857 | 9/1988 | European Pat. Off. . |
| 0 510 455 | 10/1992 | European Pat. Off. . |
| 1 238 188 | 4/1967 | Germany . |

*Primary Examiner*—Robert A. Clarke
*Attorney, Agent, or Firm*—Young & Thompson

[57] ABSTRACT

Elastic tapes consisting of non-weldable elastic warp threads and weldable thermoplastic weft threads, are fixed to one side of a cover layer of a disposable diaper by ultrasonic welding of the thermoplastic weft threads

16 Claims, 3 Drawing Sheets

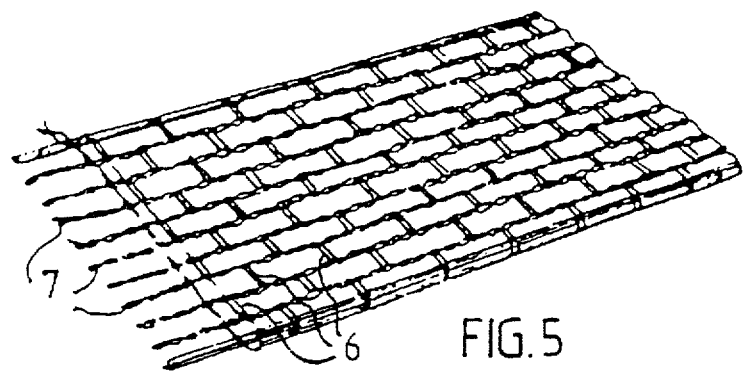
FIG.5
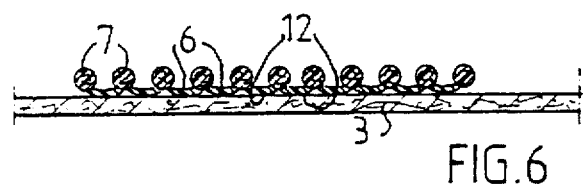
FIG.6
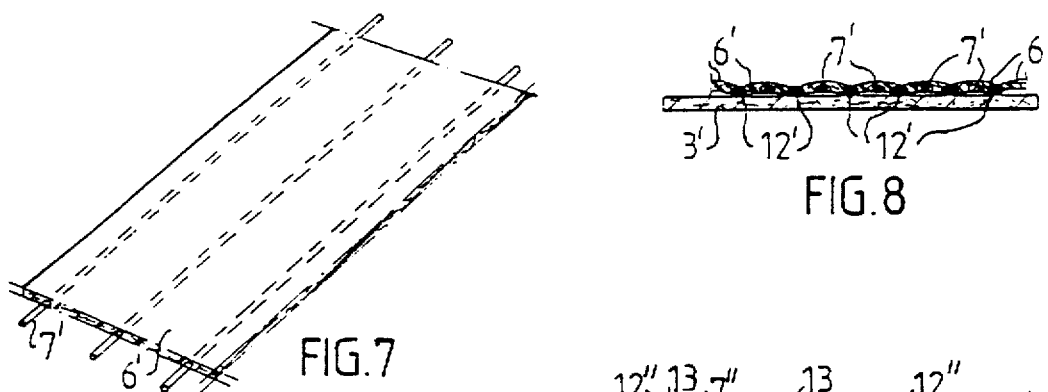
FIG.7
FIG.8
FIG.9
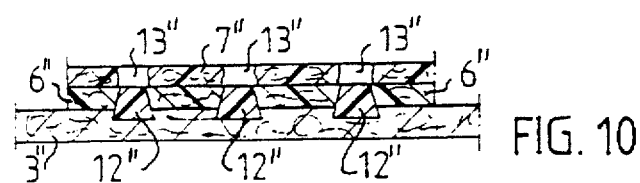
FIG.10

METHOD OF BONDING AN ELASTIC MATERIAL TO A SUBSTRATE AND ARTICLE MANUFACTURED BY SAID METHOD

This application is a 371 application of PCT/SE 94/01236, filed Dec. 21, 1994.

BACKGROUND OF THE INVENTION

The present invention relates to a method of bonding an elastic material comprising at least one elastic component and at least one thermoplastic component, to a substrate. The present invention also relates to an article comprising an elastic material and a substrate bonded therewith.

It is well known in the field to apply elastic elements to absorbent disposable products such as diapers, incontinence protectors, pant diapers and sanitary napkins to create better comformity to the user's anatomy as he or she moves. The elastic elements are usually applied along the edge portions (the leg and/or waist edge portions) in order to achieve a good seal there to prevent leakage of fluid and/or excrement from the article.. Elastic cover material for absorbent disposable articles is also known, i.e. not only separate elastic elements along the edge portion. Rather, the cover layers (the fluid receiving surface layer and/or the fluid blocking outer layer) can be completely elastic. When separate elastic elements have been applied, it is usual that they are applied between the cover layers of the article, i.e. the fluid receiving surface layer and the fluid blocking outer layer. Usually the elastic elements consist of elastic rubber threads which are anchored in place by means of adhesive, at least at their end portions.

In contrast to the traditional sandwich lamination of the elastic element between two layers, it is also known to apply, in various applications, an elastic element or, alternatively, an elastic material layer, against one side of a single layer or substrate, by gluing, for example SE 450 454 describes, for example, that a net work consisting of unspecified elastic and inelastic strands can be fixed in an unspecified manner to an additional material layer of the article. (See especially page 13, lines 19–28).

EP-A 60 405 describes an elastic tape comprising elastic threads of rubber or synthetic rubber, some of which are entwined in relatively inelastic threads of natural or artificial textile fibres. Fixing elastic tapes to substrates is not discussed at all in EP-A 60 405.

FR-A 2 452 537 describes an elastic material comprising a relatively inelastic thread, of cotton, for example, surrounded by a knitted elastic thread of rubber or Lycra®, for example. When the elastic material contracts from its extended state, loops are formed of the relatively inelastic thread between two subsequent knots or stitches on the inelastic thread. (See especially FIGS. 2 and 3). There is no indication in this specification as to how such an elastic material could be anchored to a substrate.

FR-A 2 643 925 describes an elastic material which is achieved by braiding together elastic warp threads, generally of artificial or natural rubber, and relatively inelastic weft threads. This specification does not give any indication either as to how an elastic material could be anchored to a substrate.

SUMMARY OF THE INVENTION

A primary purpose of the present invention is to be able to anchor elastic elements without using adhesive, i.e. glue.

Another purpose is to permit anchoring of elastic elements to one side of a substrate, i.e. without the necessity of applying it between two layers.

A further purpose of the present invention is to make possible bonding by welding of elastic materials which are not naturally heat-bondable or weldable to a substrate.

An additional purpose is to achieve an article of disposable character, where the materials are bonded in such a manner.

These purposes are achieved by a method of the type described by way of introduction, which is characterized in that the thermoplastic component or the thermoplastic components of the elastic material are bonded to the substrate and by an article of the type described by way of introduction which is characterized in that the elastic material comprises at least one elastic component and at least one thermoplastic component welded or thermally bonded to the substrate.

The elastic component is locked to the thermoplastic component and the thermoplastic component is bonded to a substrate, preferably by ultrasonic welding, whereby the elastic component is indirectly bonded to the substrate. The thermoplastic component thus functions as a type of bridge between the substrate and the elastic component.

An important advantage of an elastic material bonded according to the invention is that it is possible to bond an elastic material which is not weldable or thermally bondable to a substrate, by welding or thermobonding. The solution is that the bonding is effected indirectly by locking the elastic components, i.e. by means of friction or chemical adhesion, to thermoplastic components, which are in turn bonded to the substrate.

Such a bonding method according to the invention avoids completely expensive binders and the disadvantages which they bring to the manufacturing process, such as undesirable deposits on machine components and materials in the product, blockage of adhesive units, etc.

There is also a great cost advantage in being able to elastify simple material layers, without needing to apply the elastic material between two layers, as is necessary when bonding by means of adhesives, since the elastic material covered with adhesive must be covered so that the adhesive will not come into contact with other layers of material etc. in the product.

BRIEF DESCRIPTION OF THE DRAWINGS

The invention will now be described in more detail with reference to the Figures in the drawings, where

FIG. 5 shows in enlarged perspective view an elastic material, which is known per se, which can be used in the method according to the invention.

FIG. 6 shows in cross-section the material in FIG. 5 fixed to a substrate by means of ultrasonic welding according to the invention.

3

FIG. 7 shows in perspective a so-called hydroentangled elastic material, which can be used in the method according to the invention.

FIG. 8 shows in section the elastic material according to FIG. 7 fixed by welding to a substrate, according to the invention.

FIG. 9 shows in section an elastic material which consists of elastic layer and a thermoplastic layer, said material being bonded to a substrate.

Figure 11:
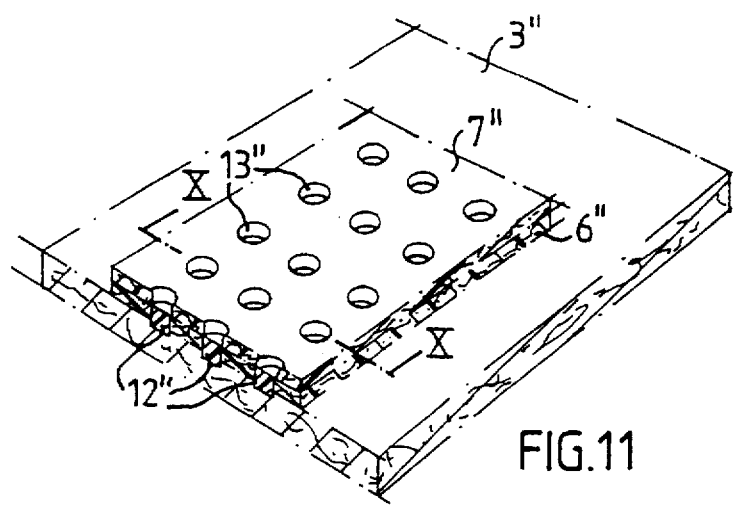

FIGS. 10 and 11 show in section and in a sectioned perspective view a bond similar to that shown in FIG. 9 but where the welding has burned holes in the elastic layer.

Figure 12:
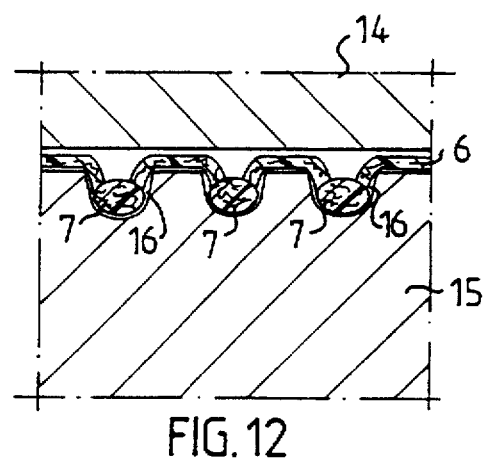

FIG. 12 shows another variant of the method according to the invention.

DESCRIPTION OF THE PREFERRED EMBODIMENT

Figure 1:
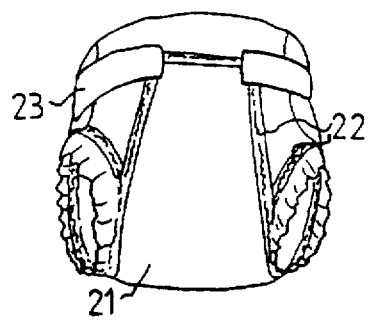
FIG. 1 shows a disposable diaper manufactured according to the method.

FIG. 1 shows a disposable diaper 21 with strips 22 of elastic material to keep the diaper tight against the body and legs of the user. The diaper is held together by pieces of tape 23. Elastic strips have been previously fixed between the cover layers of the diaper, i.e. between the fluid receiving surface layer and the fluid blocking outer layer, or which have been glued to one of the layers. In this article according to the present invention, the thermoplastic component of the elastic material is fixed according to the method of the invention, in this case to the outer layer of the diaper, by ultrasonic welding.

Figure 2:
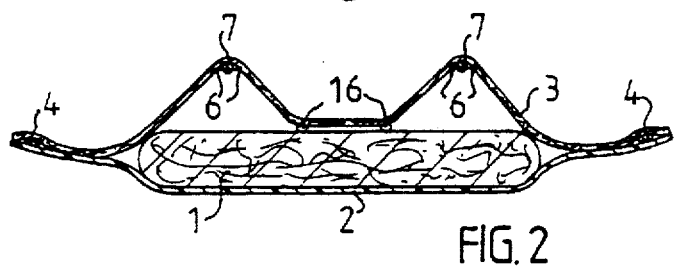
FIG. 2 shows in section the crotch portion of a diaper according to the invention.

FIG. 2 shows in cross-section the crotch portion of a diaper, with an absorbent body 1 with a fluid impermeable cover layer 2 and a fluid permeable cover layer 3 on the side facing the user. At its edges, two elastic elements 4 are applied by the traditional "Sandwich" method. Two upstanding folds are arranged in the longitudinal direction of the diaper, which folds are created by the elastic elements applied in accordance with the invention to the liquid permeable cover layer 3, said elastic elements consisting of at least one elastic component 7 and at least one thermoplastic component 6. The fluid permeable cover layer 3 is not fixed to the underlying absorbent body within the respective fold area. The elastic material in the folds has the same shape as the elastic material described in FR 2 452 537 (see FIG. 1 in this French patent specification) and which is shown in the present patent application in FIGS. 4A, 4B but fixed according to the method of the present invention to a substrate. An elastic material similar to that shown in FR 2 643 915 or any other elastic material at all which could be used within the scope of claims 1 or 8, for example coextruded or copolymerized material. In the embodiment according to FIG. 2, only the thermoplastic components 6 of the elastic material is fixed to the substrate, which in this case is the inside of the liquid permeable cover layer 3, to thereby achieve in a very simple manner a single-sided bond between the elastic material and the inside of the cover layer, without damaging the elastic component 7. The liquid permeable cover layer 3 is glued to the absorbent body 1 at the point 16.

Figure 3:
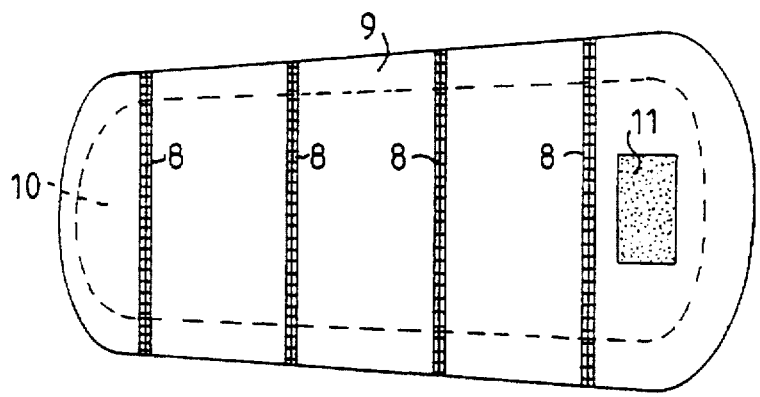
FIG. 3 shows in plan view a sanitary napkin according to the invention, FIGS. 4A and 4B, respectively, show a plan view and a cross-sectional view, respectively, of an elastic material, known per se, which is fixed to a substrate according to the invention.

FIG. 3 shows another embodiment of the invention in a sanitary napkin, where 8 designates strips of an elastic material which can be of the type shown in FIG. 5, fixed to the liquid tight cover layer 9 facing away from the body of the user, and which covers one side of the absorbent body 10. Reference numeral 11 designates an adhesive area for fixing the sanitary napkin to the underpants of the user.

Figure 4A:
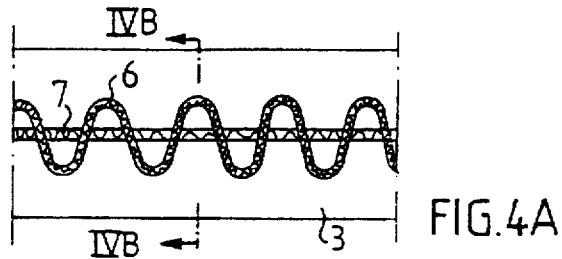
Figure 4B:
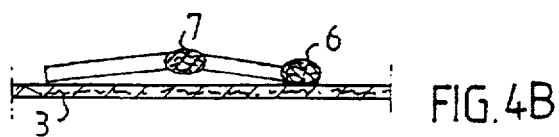

FIGS. 4A and 4B, respectively, show a plan view and a cross-sectional view, respectively, of an elastic material

4 similar to that shown in FR-A 2 452 537, which is fixed according to the method of the invention to a substrate by welds, for example. Portions corresponding to that shown in FIG. 2 have been given the same reference numerals and the numeral 7 thus designates an elastic component, in this case an elastic thread, and the numeral 6 designates a thermoplastic component which is joined to the substrate by ultrasonic welding in this case.

FIG. 5 shows an enlarged perspective view of an elastic material similar to that described and shown in FR-A 2 643 915 where non-weldable elastic longitudinal warp threads 7 are woven together with transverse weldable thermoplastic weft threads 6 to form an elastic tape, which can be fixed to a substrate by welding the thermoplastic weft threads 6 to the substrate 3 as shown in FIG. 6. The welds to the substrate 3 are made at the points 12 between and without affecting the elastic warp threads 7.

Another example of an elastic material which can be used in articles manufactured by the method according to the invention is shown in FIG. 7, a so-called hydroentangled elastic material, where 7' designates the elastic longitudinal threads which are friction locked by hydro-entangling, a method whereby loose fibres in a web are subjected to high pressure water jets and are displaced and entangled in each other as well as around the longitudinal elastic threads (in this case rubber threads), so that friction locking will occur between the elastic components and the thermoplastic components (the fibres). Welding of the thermoplastic hydroentangled fibre fabric 6' is effected in the areas between the elastic threads 7' and outside said threads at the edges. The elastic material can of course be of any length, width or number of elastic threads per unit of width.

FIG. 8 shows in cross-section such a hydroentangled elastic material fixed to a substrate 3' at welds 12' between and outside the elastic components, in this case rubber threads 7'.

Up to now, elastic materials have been described which are held together by means of friction between the elastic and the thermoplastic components. Here below will be described embodiments where an elastic material is used where the elastic and the thermoplastic components in the elastic material have been joined together by chemical adhesion, coextrusion or copolymerization. In the example of FIG. 9, an elastic material consisting of an elastic layer 7" and a thermoplastic layer 6", which chemically adhere to each other, have been joined at points 12" to a substrate 3". During the bonding process with the substrate, heated pins on a roller are moved through the holes, for example, into contact with the thermoplastic layer. The elastic layer can also have a net or grill shape, and the welding pins are inserted into the intermediate spaces into contact with the thermoplastic layer.

FIGS. 10 and 11 show a practical example where an elastic material consisting of an elastic layer 7 and a thermoplastic layer 6" have been fixed to a substrate 3". During point welding, the holes 13 have been burned through the elastic component 7" and created weld points which bond together the thermoplastic layer 6" and the substrate 3".

FIG. 12 shows a variant of the method according to the invention, whereby the elastic component, in this case longitudinal elastic threads 7, are hidden in grooves 16 in a counter roller 15 at the moment of welding in order to keep out of the way of the ultrasonic horn 14 for ultrasonic welding. The thermoplastic components 6 are arranged, however, in contact with the lateral surface of the counter roller and will be hit by the horn in the nip between it and the counter roller during welding to the substrate, which is not shown in this figure. This example is of course also applicable to purely thermal bonding, i.e. the elastic components can be hidden in grooves in a rotating roller, while the thermoplastic components are arranged outside the lateral surface of the roller, so that the latter components can come into contact with a heated second roller in the nip between the two rollers.

What is claimed is:

1. A method of bonding an elastic material, comprising at least one elastic component (7) and at least one thermoplastic component (6), to a substrate (3), only the thermoplastic component or the thermoplastic components (6) of the elastic material being bonded to the substrate (3), said elastic component being held stretched during bonding, wherein the bonding is effected by ultrasonic welding and wherein the elastic material is bonded only to said substrate (3).

2. The method according to claim 1, wherein the elastic material is held together by means of friction between the elastic components (5) and the thermoplastic components (6).

3. The method according to claim 1, wherein the elastic material is held together by the elastic components being joined to the thermoplastic components by means of chemical adhesion.

4. The method according to claim 3, wherein the chemical adhesion is effected by means of coextrusion or copolymerization.

5. The method according to claim 3, wherein the elastic and thermoplastic components of the elastic material are layers which are held together by means of chemical adhesion, and wherein the thermoplastic layer lies in direct contact with the substrate and is bonded by means of ultrasonic welding to the substrate.

6. The method according to claim 5, wherein the bonding with the substrate is effected at points.

7. The method according to claim 1, wherein the thermoplastic component(s) at or prior to bonding is (are) allowed to assume an essentially unloaded state.

8. The method according to claim 1, wherein the thermoplastic component(s) is (are) relatively inelastic.

9. The method according to claim 1, wherein the elastic component (7) or the elastic components are protected from damage during the bonding of the thermoplastic component(s) (6) of the elastic material to the substrate (3) by being moved during the bonding into depressions or spaces in means for bonding the thermoplastic component(s) (6) of the elastic material to the substrate (3).

10. The method of claim 1, wherein the elastic material is a woven mesh of elastic strands arrayed in a first direction and thermoplastic strands arrayed generally perpendicular to the first direction, and wherein the bonding of the elastic material only to the single substrate comprises the step of ultrasonically welding only the thermoplastic strands to the single substrate between the elastic strands while the elastic strands are being stretched.

11. The method of claim 1, wherein the elastic material comprises two layers, an elastic layer with openings therethrough to a thermoplastic layer that is on the single substrate, and wherein the step of bonding the elastic material only to the single substrate comprises the step of ultrasonically welding only the thermoplastic layer to the single substrate through the openings in the elastic layer while the elastic layer is being stretched.

12. The method of claim 1, wherein the elastic material comprises two components, an entangled thermoplastic layer and elastic threads friction locked within the entangled thermoplastic layer, and wherein the step of bonding the elastic material only to the single substrate comprises the step of ultrasonically welding only the entangled thermoplastic layer to the single substrate between the elastic threads while the elastic threads are being stretched.

13. An article comprising a substrate and an elastic material pretensioned and bonded therewith, in which the elastic material comprises at least one elastic component and at least one thermoplastic component, said elastic material being bonded only to said substrate, said thermoplastic component being bonded by ultrasonic welding to said substrate.

14. The article according to claim 13, wherein the thermoplastic component(s) of the elastic material is or are locked by friction by said elastic components.

15. The article according to claim 13, wherein the thermoplastic component(s) of the elastic material is or are joined by means of chemical adhesion to its elastic component(s).

16. The article according to claim 13, wherein the article is an absorbent disposable product.

* * * * *